United States Patent [19]

Kogame et al.

[11] Patent Number: 5,316,602
[45] Date of Patent: May 31, 1994

[54] METHOD FOR MANUFACTURING CERAMIC GREEN SHEET LAMINATE FOR AN ELECTRONIC COMPONENT

[75] Inventors: Toshihiko Kogame; Mitsuro Hamuro, both of Kyoto, Japan

[73] Assignee: Murata Manufacturing Co., Ltd., Japan

[21] Appl. No.: 682,346

[22] Filed: Apr. 9, 1991

[30] Foreign Application Priority Data

Apr. 19, 1990 [JP] Japan .................. 2-103530

[51] Int. Cl.⁵ .................. B32B 31/00; C09J 5/00
[52] U.S. Cl. .................. 156/64; 156/89; 156/251; 156/277; 156/306.3; 264/40.1; 264/153
[58] Field of Search .................. 156/89, 64, 251, 277, 156/306.3; 264/40.1, 510, 553, 132, 139, 153, 212

[56] References Cited

U.S. PATENT DOCUMENTS 4,771,520 9/1988 Tanaka et al. .................. 29/25.42
5,019,200 5/1991 Kawabata et al. .................. 156/264

FOREIGN PATENT DOCUMENTS 3613958 10/1986 Fed. Rep. of Germany .
0679816 9/1952 United Kingdom .
1006811 10/1965 United Kingdom .
1162927 9/1969 United Kingdom .
1419200 12/1975 United Kingdom .
2228368 8/1990 United Kingdom .

*Primary Examiner*—Jeffery Thurlow
*Assistant Examiner*—Christopher A. Fiorilla
*Attorney, Agent, or Firm*—Ostrolenk, Feber, Gerb & Soffen

[57] ABSTRACT

A long composite which includes a long carrier film and a green ceramic layer continuously formed thereon along its longitudinal direction is prepared and continuously guided successively to a printing station, a drying station and a punching station while being maintained in the long configuration. A conductor film is printed on the green ceramic layer with conductive paste in the printing station, the printed conductor film is dried in the drying station, and the green ceramic layer provided with the conductor film is punched while being registered with the conductor film and separated from the carrier film in the punching station, whereby a ceramic green sheet for a laminated ceramic electronic component is extracted.

8 Claims, 3 Drawing Sheets

METHOD FOR MANUFACTURING CERAMIC GREEN SHEET LAMINATE FOR AN ELECTRONIC COMPONENT

BACKGROUND OF THE INVENTION

1. Field of the Invention

The present invention relates to a method of and an apparatus for manufacturing a ceramic green sheet which is employed for a laminated ceramic electronic component.

2. Description of the Background Art

A laminated ceramic electronic component such as a laminated ceramic capacitor, a laminated inductor or a multilayer circuit board, for example, is obtained by stacking ceramic green sheets. A laminated ceramic capacitor, which is the most typical example of such a laminated ceramic electronic component, has generally been manufactured in the following manner:

(1) A mother sheet of green ceramic is punched into a rectangular form, to obtain a ceramic green sheet for stacking.
(2) Internal electrodes are printed on the rectangular ceramic green sheet.
(3) The printed internal electrodes are dried.
(4) A plurality of such ceramic green sheets, which are provided with internal electrodes of a first pattern, are alternately stacked with those provided with internal electrodes of a second pattern, which is different from the first pattern.
(5) The stacked green sheets are aligned on the basis of their outlines.
(6) The formed laminate of the ceramic green sheets is introduced into a die assembly and pressurized.
(7) The laminate is cut into chips for forming independent laminated ceramic capacitors. Then steps of firing the chips and forming external electrodes thereon are carried out to obtain a desired laminated ceramic capacitor.

In the aforementioned method of manufacturing a laminated ceramic capacitor, the internal electrodes are printed in the step (2) after the rectangular ceramic green sheet is obtained in the step (1). If misregistration internal electrodes with respect to the outsides of the chips will be occurs in the step of printing the internal electrodes, therefore, such misregistration of the carried over to the final product, since such ceramic green sheets are stacked on the basis of their outlines in the step (5). Thus, the laminated ceramic capacitors formed in this way are prone to have variations or statistical dispersion in their capacitance.

In the step (5), the stacked ceramic green sheets are registered by means of vibration or another known method so that the outlines thereof are aligned with each other. However, it is impossible to improve stacking accuracy since the ceramic green sheets are relatively inferior in mechanical strength. This also leads to dispersion of the acquired capacitances of the final chips, particularly in laminated ceramic capacitors.

Further, the capacitance acquired by each laminated ceramic capacitor is substantially determined at the step (2). In the step (2), the internal electrodes are printed on the ceramic green sheet which has already been punched into a rectangular outline, and such ceramic green sheets are aligned in the stacked state on the basis of the outlines in the step (5). Thus, it is impossible to arbitrarily change the capacitance acquired by the formed laminated ceramic capacitor, since the ceramic green sheets are provided with internal electrodes having the same types of patterns. In order to obtain a plurality of types of laminated ceramic capacitors having different capacitances, it is necessary to prepare a plurality of types of ceramic green sheets having different patterns of internal electrodes in the step (2).

While it is necessary to directly handle the ceramic green sheet in the steps (2) to (5), the difficulty of such handling is increased as the thickness of the ceramic green sheet is reduced.

SUMMARY OF THE INVENTION

Accordingly, an object of the present invention is to provide a method of and an apparatus for manufacturing a ceramic green sheet for a laminated ceramic electronic component, which can solve the aforementioned problems.

In order to solve the aforementioned technical problems, the present invention provides a method of manufacturing a ceramic green sheet for a laminated ceramic electronic component, which comprises the steps of preparing a long composite comprising a long carrier film and a green ceramic layer continuously formed thereon along its longitudinal direction, and continuously guiding the long composite successively to a printing station, a drying station and a punching station while maintaining the composite in an elongated configuration, backed by the carrier film. In the printing station, a conductor film is printed on the surface of the green ceramic layer with conductive paste. In the drying station, the printed conductor film is dried. In the punching station, further, the green ceramic layer provided with the conductor film is punched in a position registered with the conductor film and separated from the carrier film, whereby a ceramic green sheet for a laminated ceramic electronic component is extracted.

The present invention also provides an apparatus for carrying out the aforementioned method. This apparatus comprises a supply source for supplying a long composite comprising a long carrier film and a green ceramic layer continuously formed thereon along its longitudinal direction, a printing station for printing a conductor film on the surface of the green ceramic layer of the long composite from the supply source, with conductive paste, a drying station for drying the conductor film provided on the long composite, after it has passed through the printing station, and a punching station for punching the green ceramic layer of the long composite, after it has passed through the drying station, in a position registered with the conductor film, and separating the green ceramic layer from the carrier film, thereby extracting a ceramic green sheet for a laminated ceramic electronic component.

In order to obtain a ceramic green sheet for a laminated ceramic electronic component according to the present invention, the green ceramic layer which is formed on the long carrier film is continuously handled while being held on the long carrier film and maintained in the long configuration, from the step of printing a conductor film, such as an internal electrode, on the green ceramic layer, to the step of punching the same for extracting a ceramic green sheet.

According to the present invention, the green ceramic layer, which is subjected to various processes for obtaining a ceramic green sheet punched into prescribed dimensions and configuration, is handled while being backed by the carrier film. Thus, the carrier film advantageously makes up for small mechanical strength of the green ceramic layer. Therefore, even if the green ceramic layer has a small thickness of not more than 30 μm, for example, it is possible to manufacture a ceramic green sheet with high reliability, substantially without deformation or breakage in handling.

Further, since the green ceramic layer is continuously subjected to the desired processes while remaining in the long configuration, it is easy to maintain the cleanliness of the green ceramic layer. Thus, it is possible to easily obtain a high-quality ceramic green sheet.

Since the conductor film is printed on the green ceramic layer while the green ceramic layer is part of the long composite, and the green ceramic layer is punched in the later step to provide a ceramic green sheet having a desired geometry, it is possible to compensate for misregistration of the conductor film, which may be caused in the printing step, in the later punching step. Thus, the punched ceramic green sheet has no undesired misregistration of the conductor film. Such punched ceramic green sheets are stacked while being maintained in registration as attained in the punching step, whereby no misregistration is caused in the conductor films, such as internal electrodes, in the laminated ceramic electronic component formed in this way.

According to the present invention, further, the ceramic green sheet is punched and extracted from the green ceramic layer after the conductor film is printed on the green ceramic layer. Therefore, it is possible to easily obtain a plurality of types of laminated ceramic electronic components, such as laminated ceramic capacitors having different opposite areas of internal electrodes, i.e., different acquired capacitances, for example, by making adjustable at least either the position where the conductor film is printed on the green ceramic layer, or the position where the ceramic green sheet is punched and extracted from the green ceramic layer.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
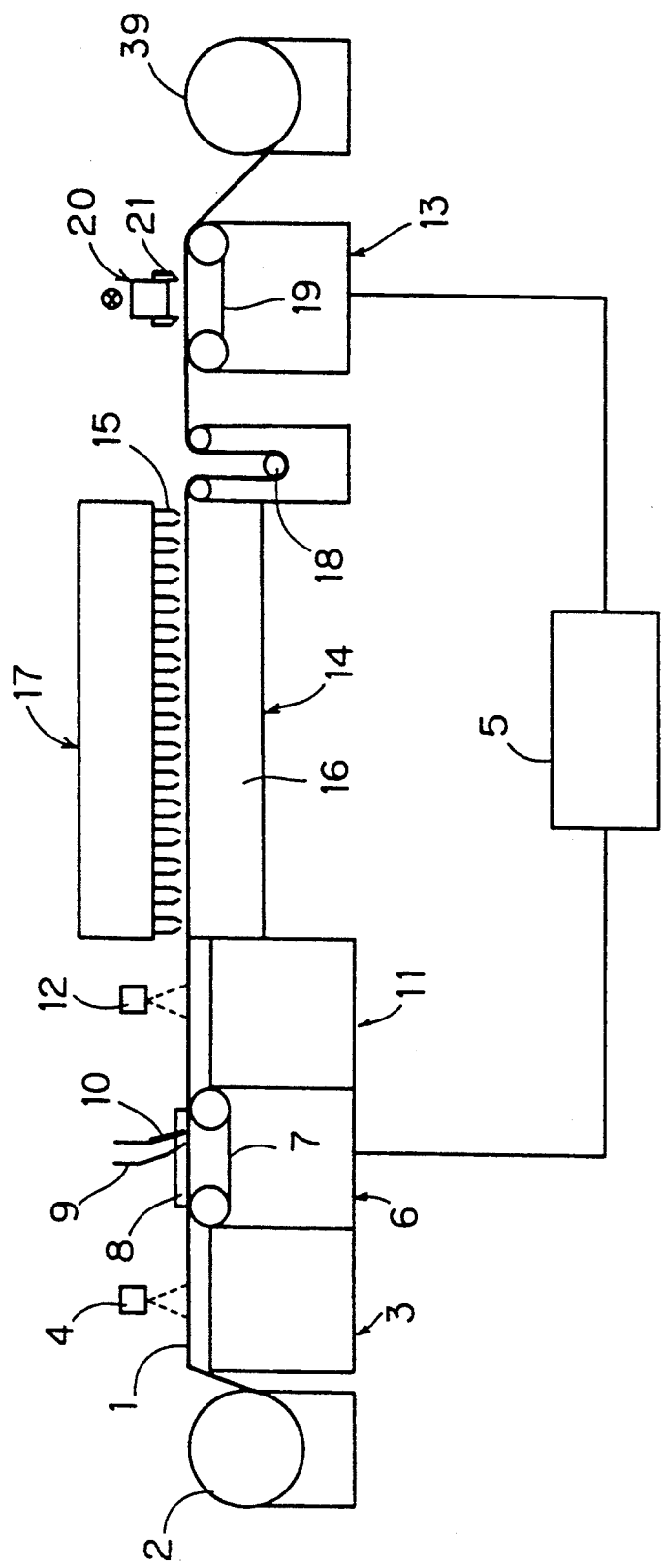
FIG. 1 illustrates an apparatus for preparing a ceramic green sheet for a laminated ceramic electronic component according to an embodiment of the present invention.

FIG. 1 illustrates an apparatus for manufacturing a ceramic green sheet for a laminated ceramic electronic component according to an embodiment of the present invention.

This apparatus comprises a supply reel 2, which is adapted to supply a long composite 1, the composite comprising a long carrier film and a green ceramic layer continuously formed thereon along its longitudinal direction. The composite 1 is drawn out from the supply reel 2 and guided to subsequent stations while the green ceramic layer faces upward. It is preferable to control the tension and the cross-directional position of the composite 1, which is drawn out from the supply reel 2.

The composite 1 is then guided to a defect detecting station 3, where any defective portions of the green ceramic layer are detected by visual observation or an optical detector 4, and information on such a defective portion is transmitted to a controller 5.

Then the composite 1 is guided to a printing station 6. The printing station 6 is provided with a conveyor 7 for carrying the composite 1, a reciprocable slider having a suction mechanism, a suction roll, or the like. In this printing station 6, a conductor film is printed on the surface of the green ceramic layer, which is contained in the composite 1, with conductive paste at a constant pitch. For this purpose, a screen 8, a scraper 9 for spreading the conductive paste on the screen 8 and a squeegee 10 for applying the conductive paste onto the surface of the green ceramic layer through the screen 8 are arranged above the conveyor 7. If the green ceramic layer defect detecting station 3 detects a defective portion of the green ceramic layer, it is preferable to print no conductor film on such a defective portion. In this printing station 6, a registration mark may be printed simultaneously with printing of the conductor film.

Then the composite 1 is guided to a defective printing detecting station 11. In this part, any defective printed portion is detected by visual observation or an optical detector 12, and information on such a defective printed portion is inputted into the controller 5. The controller 5 controls an operation in a punching station 13, which is described later, so that the defective printed portion is not used in a step when the ceramic green sheets are stacked. In this case, any shortage of printed material caused by the non-use of defective printed portions is automatically corrected by additional printing.

Then the composite 1 is guided to a drying station 14. The drying station 14 is provided with a drying furnace 17, which comprises a hot air nozzle 15 for supplying hot air to the upper surface of the composite 1 from above and a heating panel 16 for heating the lower surface of the composite 1 by heat transfer. Infrared radiation may be employed in the drying station 14, which is adapted to dry the conductor film printed in the printing station 6.

Then the composite 1 is guided around a dancer roller 18. Thus, the tension of the composite 1 is controlled between the printing station 6 and the punching station 13, which is described later, while any difference between the feed rates of the composite 1 in the printing and punching stations 6 and 13 is absorbed. Such difference of the feed rates is not accumulated since the punching of the green ceramic layer in the punching station 13 is guided by the location of the printed conductor film and the registration mark.

Figure 2:
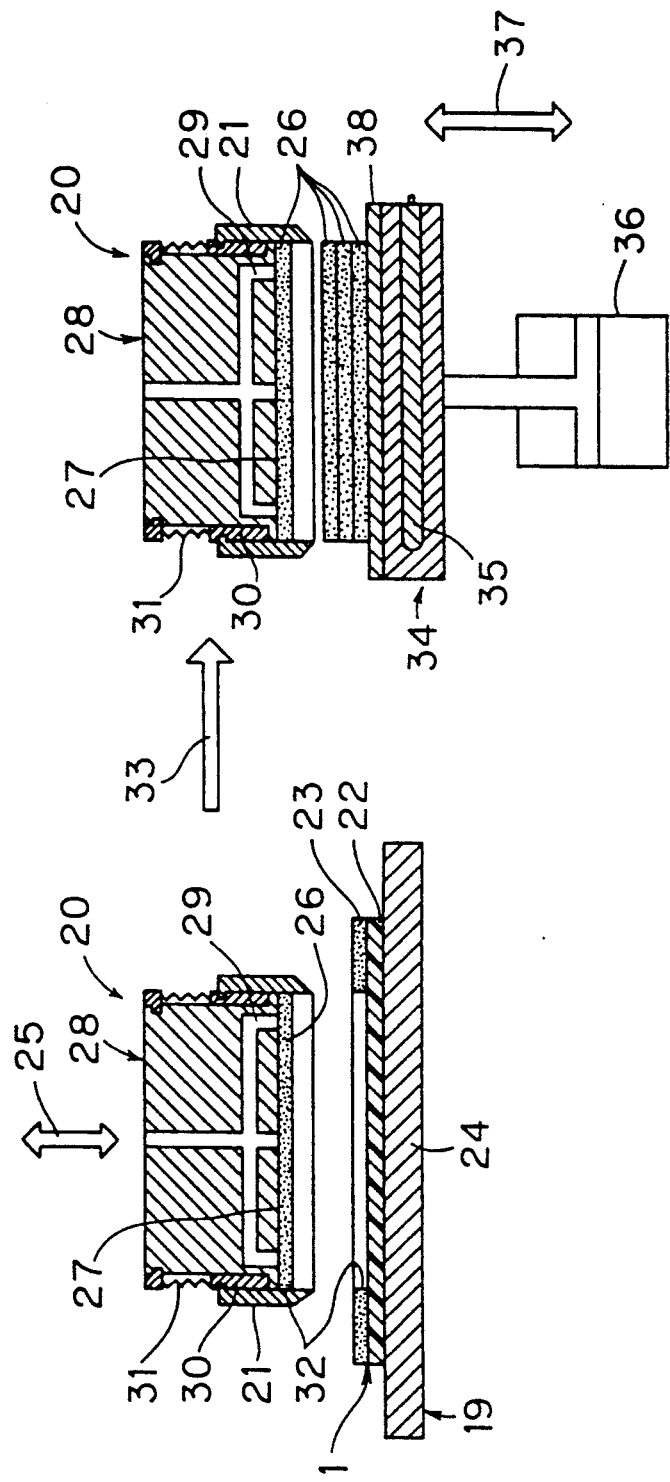
FIG. 2 is an enlarged sectional view showing an apparatus provided in a punching station 13 shown in FIG. 1.
Figure 3:
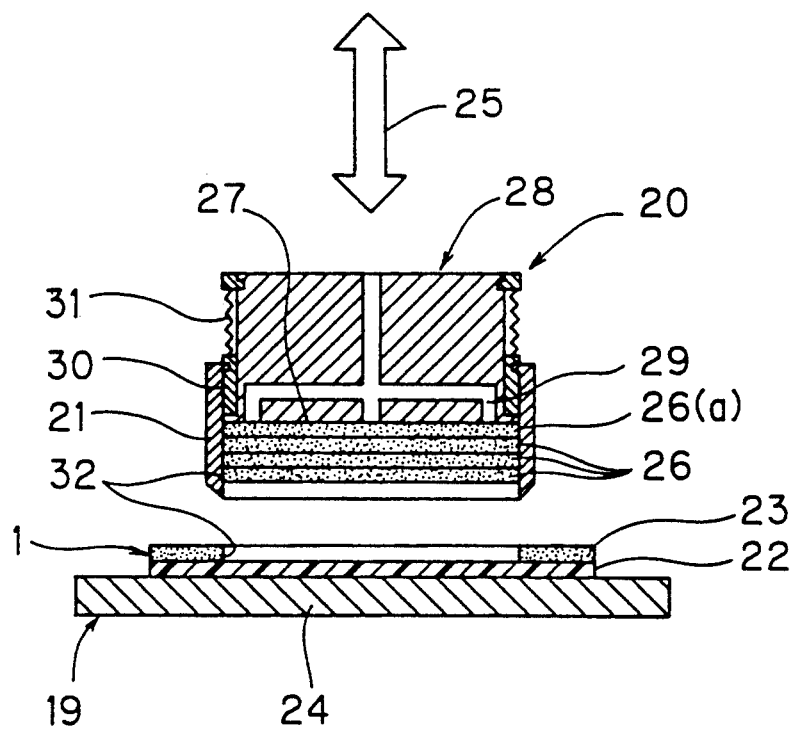
FIG. 3 is an enlarged sectional view showing an apparatus which can be substituted for the apparatus shown in FIG. 2.

Then, the composite 1 is guided to the punching station 13. The punching station 13 is provided with a conveyor 19 for carrying the composite 1, and a pickup 20 which is arranged above the conveyor 19 on the other side of the composite 1. The pickup 20 comprises a cutting edge 21 for forming a cutting line in the green ceramic layer. FIGS. 2 and 3 show the punching station 13 in detail, including respective cutting heads that can be used therein.

The left side of FIG. 2 shows a composite 1, which comprises a carrier film 22 and a green ceramic layer 23 formed thereon. The composite 1 is placed on a conveyor belt 24, which is provided in the conveyor 19 shown in FIG. 1. A large number of pores (not shown) are preferably formed in the conveyor belt 24 to supply negative pressure through such pores, in order to position the green ceramic layer 23 on the conveyor belt 24 via the carrier film 22.

The aforementioned pickup 20 is so provided above the conveyor belt 24 so that it can approach and be separated from the conveyor belt 24, as shown by an arrow 25. The pickup 20 is provided with a head 28 defining a contact surface 27, which comes into contact with one major surface of a ceramic green sheet 26 to be stacked. The aforementioned cutting edge 21 is arranged around the head 28 to enclose the contact surface 27 while projecting from the same. The head 28 is provided with a plurality of air holes 29 in the contact surface 27. The cutting edge 21 is fixedly mounted on a slider 30, which is vertically slidable in a prescribed range on the peripheral surfaces of the head 28. Compression springs 31 regularly apply downward force to the slider 30.

When the pickup 20 approaches to the conveyor belt 24, the cutting edge 21 forms a cutting line 32, defining a closed loop, along a prescribed region of the green ceramic layer 23. Then, the cutting edge 21 is moved upwardly with respect to the head 28 so that the degree of projection from the contact surface 27 is reduced to the minimum extent sufficient for forming the cutting line 32 in the green ceramic layer 23, following sliding movement of the slider 30 against elasticity of the compression springs 31. In other words, the cutting line 32 is to be formed exclusively in the green ceramic layer 23, and no such cutting line is to pass through the carrier film 22.

Then the pickup 20 is separated from the conveyor belt 24. Thus, the ceramic green sheet 26, which is defined by the region enclosed by the cutting line 32, is extracted from the green ceramic layer 23 as shown on the left side of FIG. 2. At this time, negative pressure is supplied to the air holes 29, which are provided in the head 28, for attracting the ceramic green sheet 26 which is thereby stacked onto the contact surface 27.

In order to form the cutting line 32 with the cutting edge 21, it is necessary to correctly register the position of the conductor film, printed on the green ceramic layer 23, to which the cutting edge 21 is applied. For this purpose the aforementioned registration mark, which has been printed simultaneously with the conductor film, is detected by an optical sensor, for example, to obtain information for adjusting the position of the pickup 20. The means for carrying the composite 1 is not restricted to the conveyor belt 24, but a suction slider or a suction roller may alternatively be employed. In this case, the composite 1 may be positioned on a surface plate or the like, in order to cut out the ceramic green sheet 26.

Then, the pickup 20 is moved to a position above a stacking table 34, as shown by an arrow 33.

The stacking table 34, which contains a heater 35, is vertically movable by a vertical driving unit 36, also serving as a pressure device, along an arrow 37. A lamination base 38 is arranged on the stacking table 34.

When the pickup 20 is moved above the stacking table 34 as shown on the right side of FIG. 2, the stacking table 34 is moved upwardly. Thus, several ceramic green sheets 26 that have already been placed on the lamination base 38 as shown in FIG. 2, are brought into pressure contact with the ceramic green sheet 26 that has just been brought to the table 34 by the pickup 20. The ceramic green sheets 26 on the table 34 are continuously heated by the heater 35.

Then, the stacking table 34 is downwardly moved so that the ceramic green sheet 26, which was just held by the pickup 20, is now held by the stacking table 34. At this time, positive pressure may be supplied to the air holes 29, in order to easily separate the ceramic green sheet 26 from the contact surface 27 of the pickup 20.

Thereafter the foregoing steps are repeated a desired number of times, to stack a desired number of ceramic green sheets 26 on the lamination base 38.

When the ceramic green sheet 26 carried by the pickup 20 is placed on the ceramic green sheets 26 which have already been placed on the lamination base 38 in the aforementioned step of stacking the ceramic green sheets 26, a solvent may be applied to the peripheries of the ceramic green sheets 26 at the same time positive pressure is supplied to the air holes 29, in order to fix the ceramic green sheets 26 in the stacked state. In order to fix the ceramic green sheets 26 in the stacked state even more strongly, a heating iron may be applied in the peripheral edge portions of the stacked ceramic green sheets 26, thereby applying a pressure in relation to the direction of stacking.

FIG. 3 shows an alternate apparatus, which may be substituted for the apparatus for punching and stacking the ceramic green sheet 26 shown in FIG. 2. The apparatus shown in FIG. 3 is similar to that shown on the left side of FIG. 2. Therefore, corresponding elements are indicated by similar reference numerals, to omit redundant description.

A pickup 20 shown in FIG. 3 is adapted to not only punch a ceramic green sheet 26, but also to stack such ceramic green sheets 26 by itself, without a separate stacking table 34. Thus, the degree of projection of the cutting edge 21 from the contact surface 27 is selected to be larger than that of the cutting edge 21 from the contact surface 27 in the apparatus shown in FIG. 2.

The operation of the apparatus shown in FIG. 3 is now described. First, the pickup 20 approaches to a conveyor belt 24, so that the cutting edge 21 forms a cutting line 32, defining a closed loop, along a prescribed region of a green ceramic layer 23. At this time, the cutting edge 21 is relatively upwardly displaced with respect to a head 28 so that the degree of projection thereof is sufficient for forming the cutting line 32 in the green ceramic layer 23, with sliding movement of a slider 30 against elasticity of compression springs 31.

Then, the pickup 20 is separated from the conveyor belt 24. Thus, a ceramic green sheet 26, which is defined by the region enclosed by the cutting line 32, is cut out from the green ceramic layer 23 following retraction of the pickup 20. At this time, negative pressure is supplied to air holes 29 which are provided in the head 28, so that a first ceramic green sheet 26(a) to be stacked is attracted onto the contact surface 27 and separated from the carrier film 22.

Thereafter similar steps are repeated to stack a desired number of ceramic green sheets 26 in the space enclosed by the cutting edge 21.

When the pickup 20 approaches to the conveyor belt 24 in order to punch second and following ceramic green sheets 26 from the green ceramic layer 23, i.e., to form cutting lines 32 in the green ceramic layer 23 for punching the second and following ceramic green sheets 26, a pressure of about 20 kg/cm$^2$, for example, is applied between the pickup 20 and the conveyor belt 24. The conveyor belt 24 is heated by a heater (not shown), to be maintained at a temperature of about 90° C., for example. Thus, the stacked ceramic green sheets 26 are brought into contact with each other by thermocompression bonding.

The heat applied to the conveyor belt 24 is adapted to melt a binder contained in the ceramic green sheet 26, and to increase its viscosity. Such melting of the binder contributes to improving the joining of the stacked ceramic green sheets 26, as well as to separation of the ceramic green sheets 26 from the carrier film 22.

After a desired number of ceramic green sheets 26 are stacked on the contact surface 27 of the pickup 20 in the aforementioned manner, the laminate of the ceramic green sheets 26 is extracted from the pickup 20. At this time, it is preferable to supply positive pressure to the air holes 29, in order to facilitate such extraction.

When the defective printing detecting station 11 detects a defective portion such as a defective printed portion of the conductor film coming from the printing station 6, for example, the controller 5 controls the punching station 13 not to carry out a punching operation on such a defective portion, as hereinabove described.

Referring again to FIG. 1, the composite 1 is wound on a take-up reel 39 under tension control after prescribed portions of the green ceramic layer 23 are extracted as the ceramic green sheets 26 in the punching station 13, as hereinabove described.

In the punching station 13, the cutting edge 21 may be registered with the conductor film which is provided on the green ceramic layer by numerical control etc. and the registered state may be appropriately displaced on the basis thereof, so that it is possible to arbitrarily change the acquired capacitance in a laminated ceramic capacitor, for example.

Although the present invention has been described and illustrated in detail, it is clearly understood that the same is by way of illustration and example only and is not to be taken by way of limitation, the scope of the present invention being limited only by the terms of the appended claims.

What is claimed is:

1. A method of manufacturing a laminate of ceramic green sheets for forming a laminated ceramic electronic component, comprising the steps of:
   a) preparing a long composite which comprises a long carrier film and a green ceramic layer continuously formed on only one side of the long carrier film along its longitudinal direction;
   b) continuously guiding said long composite successively to a printing station where a conductor film is printed on the surface of said green ceramic layer with conductive paste, a drying station where said printed conductor film is dried, and a punching station, while maintaining said long composite extended in said longitudinal direction with said green ceramic layer thereon;
   c) at said punching station, (1) punching said green ceramic layer and conductor film, at a predetermined location thereon with respect to the conductor film, so as to define a punched ceramic green sheet adapted for forming a laminated ceramic electronic component, and thereafter (2) lifting and separating said ceramic green sheet from said carrier film while continuously handling said ceramic green sheet and without substantially cutting said carrier film; and
   d) maintaining said continuous handling of said ceramic green sheet while stacking said ceramic green sheet at a stacking location,
   wherein said continuous handling of said ceramic green sheet is maintained by punching said ceramic green sheet with a punching head and then employing the same punching head to stack the ceramic green sheet at the stacking location, the stacking location and punching location being immediately adjacent to each other and the stacking location being on said punching head and said punching head holding said ceramic green sheet continuously following said punching step so as to form a stack with other such ceramic green sheets also held continuously after punching.

2. A method in accordance with claim 1, wherein a registration mark in a predetermined positional relation to said conductor film is printed in said printing station simultaneously with printing of said conductor film.

3. A method in accordance with claim 2, wherein said green ceramic layer is punched in said punching station at a predetermined location in with respect to said registration mark.

4. A method in accordance with claim 1, further comprising a step of guiding said composite to a defect detecting station for detecting presence or absence of a defective portion in said green ceramic layer, and a step of controlling said printing station so that no printing is carried out in said printing station on a portion where a defect has been detected in said green ceramic layer.

5. A method in accordance with claim 1, further comprising a step of guiding said composite to a defective printing detecting station for detecting presence or absence of a defective printed portion between said printing station and said punching station, and a step of controlling said punching station so that a portion where defective printing has been detected on said green ceramic layer is rejected in said punching station.

6. A method in accordance with claim 5, further comprising the step of automatically performing additional printing so as to compensate for the rejection of any defective printed portions.

7. A method in accordance with claim 1, further comprising a step of controlling said punching station to punch said green ceramic layer provided with said conductor film at a location that is selected as a function of electrical characteristics that said laminated electronic component is desired to have.

8. A method in accordance with claim 1, further comprising a step of guiding said composite to a defective printing detecting station between said printing station and said punching station for detecting any misregistration of a printed portion of the conductor film on the green ceramic layer, and a step of controlling said punching station so that where a misregistration is detected, the punching of said green ceramic layer is adjusted so as to compensate for said misregistration.

* * * * *